United States Patent
Ananthapadmanabhan et al.

[11] Patent Number: 6,083,517
[45] Date of Patent: *Jul. 4, 2000

[54] ULTRAMILD ANTIBACTERIAL CLEANING COMPOSITION FOR FREQUENT USE

[75] Inventors: Kavssery Ananthapadmanabhan, Highland Mills; Kam Chan, New York, both of N.Y.; Dale Grinstead, Lyndhurst; Carol Vincent, Wanaque, both of N.J.

[73] Assignee: Lever Brothers Company, division of Conopco, Inc., New York, N.Y.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/937,667

[22] Filed: Sep. 26, 1997

[51] Int. Cl.$^7$ .............................. A61K 9/00; A01N 25/00
[52] U.S. Cl. ............................................ 424/405; 424/400
[58] Field of Search ..................... 424/405, 400; 510/426, 235

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 4,022,834 | 5/1977 | Gundersen | 260/564 B |
| 4,053,636 | 10/1977 | Eustis, III et al. | 424/326 |
| 4,326,977 | 4/1982 | Schmolka | 252/106 |
| 4,748,158 | 5/1988 | Biermann et al. | 514/25 |
| 4,919,837 | 4/1990 | Gluck | 252/106 |
| 5,164,107 | 11/1992 | Khan et al. | 252/106 |
| 5,607,980 | 3/1997 | McAtee et al. | 514/476 |
| 5,635,469 | 6/1997 | Fowler et al. | 510/406 |

FOREIGN PATENT DOCUMENTS

| | | |
|---|---|---|
| 024 031 | of 0000 | European Pat. Off. . |
| 161 425 | 3/1985 | European Pat. Off. . |
| 2212259 | of 0000 | Germany . |
| 2627548 | of 0000 | Germany . |
| 94/05753 | of 0000 | WIPO . |
| 95/31962 | of 0000 | WIPO . |
| 95/03150 | 2/1994 | WIPO . |

*Primary Examiner*—Jose G. Dees
*Assistant Examiner*—Kathryne E. Shelborne

[57] ABSTRACT

An antibacterial cleaning composition comprising about 0.05 to about 1 wt. % of a cationic polymer having a charge density of 0.0025 or higher, about 0.2 to about 10 wt. % of an alkylpolyglucoside having a formula: $R\text{—}O(\text{-}G)_n$ wherein R is an alkyl group having from about 8 to about 22 carbon atoms, G is a saccharide residue having 5 or 6 carbon atoms and n is a number from 1–10, about 0.2 to about 5% of a zwitterionic surfactant and about 0.2 to about 5 wt. % of a biquanide compound, the composition having a pH of 7.5 or greater.

11 Claims, No Drawings

ULTRAMILD ANTIBACTERIAL CLEANING COMPOSITION FOR FREQUENT USE

FIELD OF THE INVENTION

This invention relates to a highly effective antibacterial cleaning composition which is mild enough for frequent use and which contains a selected cationic polymer, an alkylpolyglycoside, a zwitterionic surfactant and a cationic antibacterial agent in a composition having a pH of 7.5 or greater.

BACKGROUND OF THE INVENTION

Frequent handwashes are an important part of a hygiene program for health care workers and food handlers. It is not unusual for such personnel to wash their hands twenty times a day or more. Many antiseptic products used in the settings are harsh and cause significant irritation upon repeated use. This leads to poor compliance by the personnel with required handwash guidelines. Thus, the present invention provides a highly effective antibacterial cleansing composition which is mild enough for frequent use.

Biguanide compounds, such as chlorhexidine salts, are mild antibacterial agents which have a strong infinity for binding to the skin. However, several formulation issues arise when producing compositions containing chlorhexidine. Since chlorhexidine is a cation it is incompatible with anionic materials and additionally can react with the counterion of some compatible cationic compounds to form a less soluble salt leading to precipitation of the chlorhexidine.

WO 95/31962 (Gojo Industries, Inc.) describes an antibacterial cleansing composition containing a salt of chlorhexidine and at least one nonionic surfactant which does not include any polyoxypropylene/polyoxyethylene copolymers. The composition is also described as containing at least one amphoteric surfactant and quaternary ammonium surfactants may optionally be added.

Biermann et al., (U.S. Pat. No. 4,748,158) relates to the use of alkylpolyglycoside as agent used to increase the microbiocidal activity of Biguanide compounds. The resulting Biguanide compositions are useful in the oral health field, particularly in toothpaste and mouthwashes. The compositions may also contain numerous factors including nonionic, cationic, zwitterionic and amphoteric surfactants, as well as thickeners such as hydroxyethylcellulose.

WO 94/05753 owned by Henkel Corp. describes an aqueous disinfectant cleaning composition whose activity is increased by incorporating an effective amount of a compounded formula I:

wherein R is an alkyl group having from about 8 to about 22 carbon atoms, G is a saccharide residue having 5 or 6 carbon atoms; and n is a number from 1 to 10 into an aqueous composition which contains a compound of the formula II:

wherein $R_2$ is a benzyl or $C_{1-14}$ alkyl substituted benzyl group, and each of $R_3$, $R_4$, and $R_5$ is independently an alkyl group having from about 8 to about 22 carbon atoms.

U.S. Pat. No. 4,919,837 issued to Gluck describes antiseptic cleaning compositions containing the salt of chlorhexidine in combination with at least one nonionic surfactant and a carrier wherein the weight ratio of the chlorhexidine salt to the nonionic surfactant is not more than 1:7.

Bectin Dickinson owns U.S. Pat. No. 5,164,107 which describes a surgical scrub containing chlorhexidine and nonylphenoxypoly (ethyleneeoxy), ethanol surfactant in combination with other surfactant thickeners, etc. in an aqueous vehicle.

BASF owns U.S. Pat. No. 4,326,977 describing a skin cleaning compositions comprising chlorhexidine and a polyoxyethylene/polyoxybutyleneblock copolymer wherein the polyoxybutylene portion of the compound has a molecular weight of from 500 to 2000.

Accordingly, the need exists for an antibacterial composition which is highly effective for killing bacteria and other microorganisms, but which is also mild enough for frequent use in a single day.

SUMMARY OF THE INVENTION

It is therefore an object of the present invention to provide a cleansing composition which is highly effective in killing bacteria and other microorganisms and yet is mild enough for frequent use.

It is still another object of the present invention to provide an antibacterial cleaning composition which includes a biquanide, particularly a salt of chlorhexidine, an alkyl polyglycoside, at least one zwitterionic surfactant, and a cationic polymer having a charge density of 0.0025 moles per gram or higher, preferably 0.005 moles per gram or higher, and most preferably 0.05 moles per gram or higher.

The composition exhibits having a pH of 7.5 or greater. A method of using the inventive composition is also described.

It has been unexpectedly discovered that the addition of the selected cationic polymer significantly increases the antibacterial effect of the biquanidine active in a pH range higher than that thought to be effective for the antibacterial agent. Thus, not only has a highly effective antibacterial composition been discovered, but the composition may be formulated in pH ranges higher than those taught possible in the art to increase the antibacterial range of the composition.

Moreover, the inventive compositions are significantly milder than those of the prior art. They also exhibit a desirable sensory feel, thus a promoting frequent hand washing by to health care employees and food handlers preventing the spread of harmful bacteria.

PREFERRED EMBODIMENTS OF THE INVENTION

The present invention is directed toward an antibacterial composition which effectively kills bacteria and other microorganisms but is extremely mild on the user's skin even multiwash users in such settings as healthcare and food handling. The compositions of the invention have been found to significantly reduce a number of colony forming units (CFUs) of bacteria such as *staphylococcus aureus* and *Pseudomonas aeruginosa* at a pH level which increase the effectiveness of the active ingredients of the invention.

The essential ingredients for the antimicrobial cleansing composition having a pH of 7.5 or greater includes a biquanidine compound, preferably a salt of chlorhexidine, an alkylpolyglycoside, a zwitterionic surfactant such as betaine, and a cationic polymer having charge density higher than 0.0025 moles per gram.

Cationic Polymer

An effective amount of preferably about 0.05 to about 1 wt. % of a selected cationic polymer is a critical aspect of the invention Cationic charge density of the polymer can be defined either as the effective cationic charge per unit length of the polymer chain (linear charge density equals total number of charges on a polymer molecule divided by the average length of the polymer chain) or in terms of number of charges in moles per unit weight of the polymer (total number of cationic charges on a repeat unit of which the polymer is comprised of, divided by the molecular weight of the repeat unit). For the purposes of this application, we have defined the charge density of the polymer molecule in terms of number of charges per unit weight. Thus, the charge density is essentially given by:

Charge density=Total number of charges per repeat unit
Molecular weight of the repeat unit
or
Total number of charges per polymer chain Molecular weight of the polymer Examples of suitable polymers useful for the invention include polyethyleneimine ($-\{CH_2-CH_2-NH-\},-$) supplied by Rhone-Poulen under the trademark Lupasol™, having a monomer molecular weight of 43 gms. And one charge per monomer unit, has a charge density of 0.023 moles per gm. (1 divided by 43) under acidic pH conditions; polydimethyl diallyl ammonium chloride (Polyquaternium 6, $-(C_8H_{16}NaCl)_n$ supplied by Calgon under the trademark Merquat™ with a monomer molecular weight of 163.5 and one charge per monomer has a charge density of 0.0061 moles per gm; Mirapol A-15 (Polyquaternium 2) supplied by Rhone-Poulenc having two quaternary charged groups per monomer unit and a molecular weight of 373 has a charge density of 0.0054 moles per gram. In the case of modified cellulosic type polymers such as Polymer JR (Polyquaternium 10) supplied by Amerchol, the charge density may have to be estimated by polyelectrolyte titration techniques or by estimating the amount of surfactant required to cause all the polymer to precipitate. Charge density of Polymer JR estimated in this manner is around 0.00175 moles per gram.

The molecular weight of the polymer is 300 to 500,000 daltons, preferably 2000 to 250,000, most preferably 5000 to 100,000.

Biquanide Compounds

As examples of the microbiocidal agents which can be used in combination with the alkyl glycosides according to the present invention there can be mentioned antiseptic bi de compound. % such as chlorhexidine (which is the common name for the antiseptic 1,1'-hexamethylene-bis-[5-(4-chlorophenyl)-biguanide], widely used in the form of its salts (such as the acetate, hydrochloride, and gluconate salts) in the cosmetic and pharmaceutical fields and also in cleaning preparations). Other known biguanide-based disinfectants are, for example, the salts of polyhexamethylene biguanide compounds having the following general formula:

Numerous antimicrobial biguanide compounds which can be used in the present invention are mentioned in the patent literature, including, for examples, European Patent No. 24,031; U.S. Pat. Nos. 2,684,924; 2,990,425; 3,468,898; 4,022,834 and 4,053,636; and German patent Nos. 2,212, 259 and 2,627,548. Additional examples of antimicrobial biguanide compounds, which can be utilized in the present invention include $N^1$-(4-chlorobenzyl)-$N^5$-(2,4-dichlorobenzyl)-biguanide; p-chlorophenyl biguanide; 4-chlorobenzhydryl biguanide; N-3-lauroxypropyl-$N^5$-p-chlorobenzyl biguanide; $N^1$-p-chlorophenyl-$N^5$-lauryl biguanide and the non-toxic addition salts thereof, especially gluconates and acetates.

A salt of chlorhexidine is selected for its antibacterial activity for the active ingredients of the present invention. The salt is present in a range of about 0.2 to 5% by weight, preferably 0.5 to 4.5% by weight, and most preferably 1 to 4% by weight. It is appreciated that for purposes of this invention all percentages recited herein are based on the percent active by way of the composition unless otherwise indicated.

Any salt of chlorhexidine which is soluble in water or another non-alcohol solvent may be used in the composition of the present invention. Such salts include gluconate, acetate, formate, lactate, isethionate, succinamate, glutamate, mono-diclycollate, dimethane sulfonate, di-isobutyrate, glucoheptonate. Preferably, the chlorhexidine salts are gluconate and acetate, the most preferred being chlorhexidine digluconate.

Alkylpolyglycoside

Present in the invention is an amount of alkylpolyglycoside having a formula: $R-O(-G)_n$
wherein R is an alkyl group having from about 8 to about 22 carbon atoms, G is a saccharide residue having 5 or 6 carbon atoms and n is a number from 1–10.

Alkylpolyglycoside in the invention are described in WO 94/05753 and U.S. Pat. No. 4,748,158, both owned by Henkel and hereby incorporated by reference. Specifically, the alkylpolyglucoside compounds are commercial surfactants and are available, for example, from Henkel Corporation, Hoboken, N.J., under the trademark names APG®, Plantaren™, or Glucopon™ and from Seppic (France) under the trademark Oramix™. Examples of such surfactants include but are not limited to:

1. an alkylpolyglycoside in which the alkyl group contains 8 to 10 carbon atoms,
2. an alkyl polyglycoside in which the alkyl group contains 9 to 11 carbon atoms.
3. Gluopon™ 625—an alkyl polyglycoside in which the alkyl groups contains 12 to 16 carbon atoms,
4. APG™ 300—an alkyl polyglycoside substantially the same as the 325 product above but having a different average degree of polymerization,
5. Glucopon™ 600—an alkylpolyglycoside substantially the same as the 625 product above but having a different average degree of polymerization,

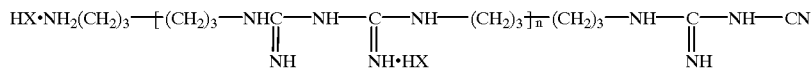

in which HX is the salt-forming acid component, such as HCl, for example, and n is a number having a value of at least 2, and preferably having a value of from about 4.5 to 6.5.

6. Plantaren™ 2000—a $C_{8-16}$ alkyl polyglycoside,
7. Plantaren™ 1300—a $C_{12-16}$ alkyl polyglycoside,
8. Plantaren™ 1200—a $C_{12-16}$ alkyl polyglycoside,
9. Oramix NS10.

The alkylpolyglucoside is present in the invention in a weight ratio about equal to the salt of the chlorhexidine, generally in the range of about 0.2 to about 10%, preferably 1 to about 5%, most preferably 1 to about 3%.

Zwitterionic Surfactant

Useful zwitterionic surfactants for the present invention are well known in the detergent art and are described at length in "Surface Active Agents in Detergents", Vol. 2, by Schwartz, Perry and Birch, Interscience Publishers, Inc. 1959, herein incorporated by reference.

In the preferred embodiments the zwitterionic or amphoteric surface active agents are agents having a betaine or sultaine structure corresponding a general formula selected from the group consisting of:

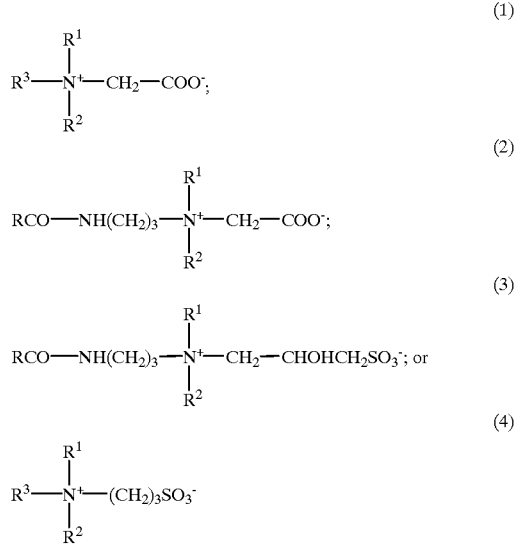

where $R^1$ and $R^2$ are the same or different and are selected from the group consisting of an alkyl radical having about 1 to 4 carbon atoms and a hydroxyalkyl radical having about 2 to 3 carbon atoms and, preferably, both being methyl groups;

$R^3$ is an alkyl radical having about 8 to 18 carbon atoms; and

R is an alkyl radical having about 7 to 17 carbon atoms; R and its bonded carbonyl group (RCO—) is preferably derived from a $C_{12}$–$C_{18}$ fatty acid. Preferred $C_{12}$–$C_{18}$ fatty acids are lauric acid, myristic acid, stearic acid, tallow acids or coconut fatty acids.

Example betainic agent of formula (1) are alkylbetaines where the alkyl group is derived from coconut fatty acids or tallow acids. Suitable alkylbetaines are given the respective means of Coco-betaine and Dihydroxyethyl tallow glycinate in the *CTFA Cosmetic Ingredient Dictionary* (hereinafter "*CTFA Dictionary*"), 3rd ed., 1982, published by the Cosmetic, Toiletry and Fragrance Association and in the *Cosmetic Bench Reference encyclopedia of cosmetic materials* (hereinafter "*Bench Reference*"), Cosmetics & Toiletries, 1984 edition, August 1984, and its addenda, December 1984 the disclosures of which are incorporated herein by reference.

Particularly preferred alkylbetaines are the coco-betaines available under the trademark designations LONZAINE 12C from Lonza, Inc., Fairlawn, N.J. and SCHERCOTAINE CB from Scher Chemicals, Inc., Clifton. N.J.

An example of a betainic agent of formula (2) is an alkylamidobetaine where the alkyl radical and its bonded carbonyl group (RCO—) are preferably derived from a fatty acid, such as lauric acid, myristic acid, stearic acid, tallow acids or coconut fatty acids. Suitable alkylamidobetaines are given the respective names lauramidopropyl betaine, myristamidopropyl betaine, stearamidopropyl betaine and cocamidopropylbouine in the *CTFA Dictionary*. Particularly preferred alkylamidobetaines are available under the trademark designations Rewoteric AMB13, AMB14, AMB14LS supplied by Witco, and Tegobetaine E supplied by Goldschmidt.

An example of a sultaine of formula (3) is one in which the alkyl radical R and its bonded carbonyl group (RCO—) are preferably derived from a fatty acid such as lauric acid, stearic acid, tallow acids, coconut fatty acids and the like. A particularly preferred sultaine is an alkylamidopropylhydroxypropylsulfobetaine where the alkyl radical R contains about 7 to about 17 carbon atoms, and where R and its bonded group (RCO—) are preferably derived from coconut fattys. An illustrative sultaine is given the name cocamidopropylhydroxysultaine in the *CTFA Dictionary* and in the *Bench Reference*.

Particularly preferred sultaines are available under the trademark Varion CAS from Sherex Chemical Company, Inc., subsidiary of Schering A. G., Dublin, Ohio, and Mirataine CBS from Rhone-Poulenc Inc., Cranbury, N.J.

An example of sultaine agent of formula (4) is an alkylsultaine in which the quaternized nitrogen atom is bonded directly to a carbon atom of an alkyl moiety preferably derived from coconut fatty acids. A suitable alkylsultaine is given the name cocosultaine in the *CTFA Dictionary* and in the *Bench Reference*.

Preferred zwitterionic surfactants are present in an amount of 0.2 to about 5%, preferably 0.5 to about 3%, most preferably 0.5 to about 2%.

pH Range

It was unexpectedly discovered that not only does the combination of the biquanide compounds with the selected cationic polymers of the invention significantly increased the activity of the antibacterial active but further alters the activity and chemical stability profile of the compounds. In aqueous solutions, chlorhexidine salts in particular generally display a maximum biological activity and chemical stability within a pH range of 5–8. The compositions of the invention exhibit maximum biological activity and stability in a pH range of 7.5 and greater, preferably 7.5 to 10, most preferably 7.75 to 9.

Salt Content

In the preferred embodiments, the final composition should exhibit a relatively low salt content for the stability of the compositions.

Additional Polymers

In the preferred embodiments, additional cationic, nonionic or zwitterionic polymers may be incorporated into the formulations to provide desirable, tactile and sensory characteristics of the products.

Optional Ingredients

The composition may also include other additives such as thickeners, emollients, quaternary ammonium surfactants, foaming agents, fragrances, coloring agents, preservatives, fungicides, pacifying agents, pearlizing agents, vitamins and the like. For example, the composition may include a polymer viscosifier or thickener such as hydroxyethyl cellulose to make the composition more stable. Samples of other suitable polymer viscosifiers include, but are not necessarily limited to hydroxypropylcellulose, methylcellulose and carboxymethylcellulose. Each additive, when present, is added in amounts up to 0.5% by weight, preferably 0.001 to about 10% by wt., most preferably 0.01 to about 5% by wt.

The balance of the composition is typically water or another non-alcohol solvent so as to provide 100% by weight of a composition.

The antimicrobial cleaning composition of the present invention is generally prepared by dissolving the various ingredients such as the alkylpolyglucoside, the zwitterionic surfactant, the soluble salt of chlorhexidine, and the selected cationic polymer in water with stirring. Any viscosifier has been preferably added and the solution been mixed until it is completely hydrated. The pH is checked and adjusted with acid or base, if necessary. Any acid or base compatible with the components of the formulation can be used, Preferred acids include citric acid, phosphoric acid, gluconic acid, lactic acid, acetic acid, and glycolic acid with citric acid and phosphoric acid being most preferred. Preferred bases include sodium hydroxide, potassium hydroxide, and triethanolamine with sodium hydroxide being the most preferred. This process can be employed with or without the application of heat to enhance the solution.

EXAMPLE 1

To compare the antibacterial activity of prior art samples (Sample A–C, E–F) and the inventive samples (D, G), base formulations were prepared containing 2% alkylpolyglucoside, 1% cocamidopropylbetaine, 2.2 wt. % PEG 6000 distearate, 10% glycerin and phosphoric acid or citric for pH adjustment. The polyethylenimine and pH was varied as follows:

| Samples | pH   | Chlorhexidine | Polyethylenimine[1] |
|---------|------|---------------|---------------------|
| A       | 7.25 | 5             | 0                   |
| B       | 7.75 | 5             | 0                   |
| C       | 7.25 | 5             | 0.25                |
| D       | 7.75 | 5             | 0.25                |
| E       | 7.75 | 4             | 0                   |
| F       | 7.75 | 4             | 0.25                |
| G       | 8.94 | 4             | 0.25                |

[1]Supplied as Lupasol P (50% active) by BASF.

EXAMPLE 2

The antibacterial activities of the samples prepared in Example 1 were determined in the DGHM test as follows:

Test organisms used in DGHM tests were *Staphylococcus aureus* ATCC 6538, *Escherichia coli* ATCC 11229, *Proteus mirabilis* ATCC 14153, and *Pseudomonas aeruginosa* ATCC 15442. The neutralizer system used is 10% Tween 80 and 1.4% lecithin.

Performance Standards

Decontamination The hand decontamination guideline includes three different in vitro tests, The first two tests are intended to provide information necessary to perform subsequent tests. The second and third tests have performance standards associated with them. The first in vitro test is a determination of the bacteriostatic and fungistatic effectiveness of the personal wash product as well as of suitable inactivating substances. This test indicates the effectiveness of the neutralizer system and it provides an indication of the minimum inhibitory concentration for the test product. The second test is the qualitative suspension test. The goal of this test is to determine the concentration of a test product above which the test organisms are completely eliminated and to identify the Gram negative test organisms is most resistant to the product and should be used in the final test. The performance standard associate with the second test is that ". . . None of the microorganism species tested are insensitive to the agent in the qualitative suspension test; all test microorganisms must be completely inactivated by the concentrate within the exposure time (15 sec or 30 sec) required for the process."[2] The third in vitro test is the quantitative suspension test and includes only *S. aureus* and the most resistant Gram negative as determined by the qualitative test. The performance standard associated with the quantitative suspension test is a 3.5 log reduction in a 75% solution of the test material within the 15 or 30 second exposure time.

[2] Guidelines for testing and evaluation of chemical disinfection methods. 1989. Deutsche Gesellschaft fur Hygiene und Mikrobiologie.

Disinfection The hand disinfection guideline in vitro methods are similar to the decontamination methods. The primary differences are increased exposure times (30 and 60 seconds) and performance standards (a 5 log reduction within 30 or 60 seconds).

Bacteriostatic and Fungistatic Test

Five ml portions of test product are added to 5 ml of 2× triptych soy broth (TSB) with and without 20× neutralizers. The tubes are inoculated with 0.1 ml of a 24 hr TSB culture of test organism and incubated for 48 hr at 34° C. The tubes are observed visually for growth. If the test product causes precipitation within the tubes, samples from the tubes were swabbed onto Lever Microbial Content Test Agar (LMCTA, MCTA+10% dextrose) and incubated at 34° C. for 24 hr.

Qualitative Test

A 0.1 ml portion of a 24 hr TSB culture or cell suspension, prepared by scraping cells from the surface of a tryptic soy agar (TSA) plate and resuspending them in sterile water, was added to the test material. The concentration of test material was generally 100% although it could be reduced if undiluted product yielded no survivors at the shortest exposure time. Samples are taken at 30 seconds, 1 , 2, and 5 minutes and inoculated into TSB with 10× neutralizer, incubated for 48 hr at 34° C., and observed visually for growth.

Quantitative Test

Identical to the qualitative test except that the bacteria in the samples taken at appropriate time intervals are enumerated by pour plating onto microbial content test agar. All dilutions were carried out in Butterfiled's buffer with 20× neutralizer. The difference between the log CFU/ml of controls and the log CFU/ml surviving in the sample is determined and reported as the reduction in log CFU/ml vs. controls. The product was tested at 100% with and without 0.2% Bovine Serum Albumin (BSA) for the disinfection test and at 75% without BSA for the decontamination test. Samples were taken at 30 seconds and 1 minute for disinfection testing and at 30 seconds for decontamination testing.

Modified DGHM Test

A modified DGHM test was used to rapidly screen multiple samples. The modified test was an abbreviated DGHM quantitative suspension test. The standard test was simplified by limiting the test to one or two organisms, generally *S. aureus* and a Gram negative. BSA was not used in the disinfection testing. In other respects it was run using the techniques described for the DGHM quantitative test. The bacteriostatic-fungistatic test was not run, nor was the qualitative suspension tests.

The remainder of the examples should demonstrate that the samples according to the invention containing the polyethyleimine was significantly more active than those without the cationic. Additionally, the pH ranges above 7.5 and particularly above 8 should also show increased activity.

EXAMPLE 3

Decontamination Test

Reduction in log CFU/ml
30 seconds contact time @ 75% dilution of formulation

| Samples | S. Aureus | P. Aeruginosa |
|---|---|---|
| A | 1.18 | 4.77 |
| B | 3.90 | >5.25 |
| C | >5.18 | 3.38 |
| D | >5.18 | >5.25 |

EXAMPLE 4

Disinfection Test

Reduction in log CFU/ml
60 seconds contact time @ 100% of formulation

| Samples | S. Aureus | P. Aeruginosa |
|---|---|---|
| E | 2.48 | >5.00 |
| F | >5.00 | 3.62 |
| G | >5.00 | >5.00 |

We claim:

1. An antibacterial cleaning composition comprising
   a) about 0.05 to about 1 wt. % of a cationic polymer having a charge density of 0.0025 or higher;
   b) about 0.2 to about 10 wt. % of an alkylpolyglucoside having a formula: R—O(-G), wherein R is an alkyl group having from about 8 to about 22 carbon atoms, G is a saccharide residue having 5 or 6 carbon atoms and n is a number from 1–10;
   c) about 0.2 to about 5 wt. % of a zwitterionic surfactant;
   d) about 0.2 to about 5 wt. % of a biquanide compound; and
   e) at least one additive selected from the group consisting of a thickener, emollient, quaternary ammonium surfactant, foaming agent, fragrance, coloring agent, preservative, fungicide, pacifying agent, pearlizing agent and vitamin,
the composition having a pH of 7.5 or greater.

2. An antibacterial cleaning composition according to claim 1 wherein the cationic polymer has a molecular weight of 300 to 500,000 daltons.

3. An antibacterial cleaning composition according to claim 2 wherein the cationic polymer is selected from the group consisting of polyethylemeimine, polydimethyl diallyl ammonium chloride, polyquaternium 2, a modified cellulosic polymer and mixtures thereof.

4. An antibacterial cleaning composition according to claim 1 wherein the biquanide compound is a salt of chlorhexidine selected from the group consisting of gluconate, acetate, formate, lactate, isethionate and succinamate.

5. An antibacterial cleaning composition according to claim 1 wherein the zwitterionic surfactant is a compound having a betaine or sultaine structure.

6. A method of cleaning a surface with an antibacterial cleansing composition comprising the step of applying to the surface a composition comprising:
   a) about 0.05 to about 1 wt. % of a cationic polymer having a charge density of 0.0025 or higher;
   b) about 0.2 to about 10 wt. % of an alkylpolyglucoside having a formula: R—O(-G)$_n$ wherein R is an alkyl group having from about 8 to about 22 carbon atoms, G is a saccharide residue having 5 or 6 carbon atoms and n is a number from 1–10; and
   c) at least one additive selected from the group consisting of a thickener, emollient, quaternary ammonium surfactant, foaming agent, fragrance, coloring agent, preservative, fungicide, pacifying agent, pearlizing agent and vitamin.

7. An antibacterial cleaning composition according to claim 1 wherein the cationic polymer has a molecular weight of 300 to 500,000 daltons.

8. An antibacterial cleaning composition according to claim 2 wherein the cationic polymer is selected from the group consisting of polyethylemeimine, polydimethyl diallyl ammonium chloride, polyquaternium 2, a modified cellulosic polymer and mixtures thereof.

9. An antibacterial cleaning composition according to claim 1 wherein the biquanide compound is a salt of chlorhexidine selected from the group consisting of gluconate, acetate, formate, lactate, isethionate and succinamate.

10. An antibacterial cleaning composition according to claim 1 wherein the zwitterionic surfactant is a compound having a betaine or sultaine structure.

11. A method according to claim 6 wherein the surface is a skin surface.

* * * * *